United States Patent [19]

Chipkin et al.

[11] Patent Number: 4,614,743

[45] Date of Patent: * Sep. 30, 1986

[54] METHODS OF TREATING PAIN AND INFLAMMATION WITH 4,7-DIMETHYL-2-(4-PYRIDINYL)-1,2,4,-TRIAZOLO[1,5-A]PYRIMIDIN-5(4H)-ONE OR THE PHARMACEUTICALLY ACCEPTABLE SALTS OR SOLVATES THEREOF

[75] Inventors: Richard E. Chipkin, Bloomfield; Joseph T. Witkowski, Morris Township, Morris County, both of N.J.

[73] Assignee: Schering Corporation, Kenilworth, N.J.

[*] Notice: The portion of the term of this patent subsequent to Feb. 5, 2002 has been disclaimed.

[21] Appl. No.: 566,093

[22] Filed: Dec. 27, 1983

[51] Int. Cl.[4] .................. A61K 31/505; C07D 487/04
[52] U.S. Cl. ..................................... 514/258; 544/263
[58] Field of Search .................. 544/263; 424/251; 514/258

[56] References Cited

U.S. PATENT DOCUMENTS

| | | | |
|---|---|---|---|
| 2,553,500 | 5/1951 | Harsh | 544/263 X |
| 3,271,401 | 9/1966 | Williams | 544/263 |
| 4,036,840 | 7/1977 | O'Brien et al. | 424/251 X |
| 4,497,814 | 2/1985 | Witkowski | 514/258 |

FOREIGN PATENT DOCUMENTS 1070243  6/1967  United Kingdom ............... 544/263

*Primary Examiner*—Donald G. Daus
*Assistant Examiner*—D. G. Rivers
*Attorney, Agent, or Firm*—Gerald S. Rosen; Stephen I. Miller

[57] ABSTRACT

The compound 4,7-dimethyl-2-(4-pyridinyl)-1,2,4-triazolo[1,5-a]pyrimidin-5(4H)-one and the pharmaceutically acceptable salts thereof are analgesic and anti-inflammatory agents. Methods for preparing and using the compound and salts are described.

8 Claims, No Drawings

METHODS OF TREATING PAIN AND INFLAMMATION WITH 4,7-DIMETHYL-2-(4-PYRIDINYL)-1,2,4,-TRIAZOLO[1,5-A]PYRIMIDIN-5(4H)-ONE OR THE PHARMACEUTICALLY ACCEPTABLE SALTS OR SOLVATES THEREOF

SUMMARY OF THE INVENTION

The invention sought to be patented in its chemical compound aspect is 4,7-dimethyl-2-(4-pyridinyl)-1,2,4-triazolo[1,5-a]pyrimidin-5(4$\underline{H}$)-one having the structural formula:

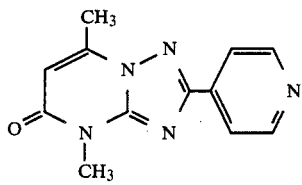

and the pharmaceutically acceptable salts thereof.

The invention sought to be patented in its pharmaceutical composition aspect is a composition which comprises 4,7-dimethyl-2-(4-pyridinyl)-1,2,4-triazolo[1,5-a]pyrimidin-5(4$\underline{H}$)-one or a pharmaceutically acceptable salt thereof, in combination with a pharmaceutically acceptable carrier.

The invention sought to be patented in its first pharmaceutical method aspect is a method for treating pain in a mammal which method comprises administering an effective amount of the above-defined pharmaceutical composition to said mammal.

The invention sought to be patented in its second pharmaceutical method aspect is a method for treating inflammation in a mammal which method comprises administering an effective amount of the above-defined pharmaceutical composition to said mammal.

DESCRIPTION OF THE INVENTION

The compound 4,7-dimethyl-2-(4-pyridinyl)-1,2,4-triazolo[1,5-a]pyrimidin-5(4$\underline{H}$)-one may be prepared by condensing 5-(methylamino)-3-(4-pyridinyl)-1$\underline{H}$-1,2,4-triazole with an acetoacetic acid ester, for example ethyl acetoacetate. This condensation is known to produce two isomeric products. The production of the desired isomer may be maximized by performing the condensation without the use of a solvent. For example in a preferred method, a 2 to 5 molar excess of the acetoacetic acid ester may be utilized in place of a solvent.

The starting material, 5-(methylamino)-3-(4- pyridinyl)-1$\underline{H}$-1,2,4-triazole may be prepared by known methods. For example, methods described in Acta Chemica Scandinavica, 19, 1135 (1965) and art recognized modifications thereof may be utilized.

The compound of the invention, 4,7-dimethyl-2-(4-pyridinyl)-1,2,4-triazolo[1,5-a]pyrimidin-5(4$\underline{H}$)-one can form salts with pharmaceutically acceptable acids such as hydrochloric, methanesulfonic, sulfuric, phosphoric and the like. The salts are prepared by contacting the free base form with a sufficient amount of the desired acid to produce a salt in the conventional manner. The free base form may be regenerated by treating the salt forms with a base. For example, dilute aqueous base solutions may be utilized. Dilute aqueous sodium hydroxide, potassium carbonate, ammonia, and sodium bicarbonate solutions are suitable for this purpose. The free base form differs from the respective salt forms somewhat in certain physical properties such as solubility in polar solvents, but the salts are otherwise equivalent to the respective free base form for purposes of the invention.

The compound of the invention and its corresponding salts can exist in unsolvated as well as solvated forms, including hydrated forms. In general, the solvated forms, with pharmaceutically acceptable solvents such as water, ethanol and the like are equivalent to the unsolvated forms for purposes of the invention.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethyl-cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in weater with viscous material, i.e., natural or synthetic gums, resins, methylcellulose, sodium carboxymethyl-cellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerne, propylene glycol and the like as well as mixtures thereof. Naturally, the solvent utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these packaged form.

The quantity of active compound in a unit dose of preparation may be varied or adjusted from 1 mg to 1000 mg according to the particular application and the potency of the active ingredient. The compositions can, if desired, also contain other therapeutic agents.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The analgesic effect of the compound of the invention 4,7-dimethyl-2-(4-pyridinyl)-1,2,4-triazolo[1,5-a]pyrimidin-5(4H)-one, (Compound) was measured using two methods that have been well-described in the literature as indicative of pain-relieving efficacy. First, the Compound was evaluated for its ability to block writhing induced by the intraperitoneal injection of a noxious agent (acetic acid). This method has been described by others (see references, infra). Briefly, groups of five mice (CF1 male, 20–26 g) were injected intraperitoneally with 0.6% aqueous acetic acid (10 ml/kg) at fifteen minutes after the oral administration of various doses of either the Compound or vehicle (0.4% aqueous methylcellulose, injection volume was 20 ml/kg po). The mice were then placed in a large observation beaker, and the number of writhes for each animal was counted during a 10 minute period three minutes after the acetic acid treatment. (A writhe is defined as a sequence of arching of the back, pelvic rotation and hindlimb extension.) A mouse was considered protected if it had 50% less incidence of writhes than the average of the concomitantly run vehicle control group. At each drug dose the number of mice protected was divided by the total number of mice in the group at that dose and multiplied by 100% to give the Percent Protected for that dose. These data were used to determine the $ED_{50}$ and 95% confidence limits according to Litchfield and Wilcoxon (infra).

The second test used to determine the analgesic effects of the Compound was the rat yeast-paw test (Randall and Selitto, infra). Male, Sprague-Dawley rats (150–200 g) from Charles River Breeding Laboratories Inc. (Wilmington, MA) were used throughout. Groups of rats were first tested for their reaction times to withdraw from pressure applied with an accelerating (20 mm Hg/sec) bullet-shaped piston to each rear paw (preyeast reaction time). Subsequently, the right rear paw was inflamed by a subplantar injection (0.1 ml) of a 20% Brewer's yeast solution (w/v in distilled $H_2O$). Sixty minutes later the latency to withdrawal was measured again (postyeast reaction time). The Compound or vehicle was then administered and reaction times were redetermined at appropriate intervals (postdrug reaction times). A 15-sec cutoff was employed.

The $ED_{7sec}$ was defined as that dose needed to increase the response latencies of the inflamed paws to 7 seconds. This time was chosen because it is the approximate response latency of a normal, non-inflamed paw. In comparison, the latency of the inflamed paw of a vehicle-treated rat was approximately 1.5 sec. The $ED_{7sec}$ and its 95% confidence limits were calculated using a regression analysis according to Brownlee (infra).

The $ED_{50}$ of the Compound in the mouse acetic acid writhing test was determined to be 34.0 (10.2, 56.6)*mg/kg po.

The $ED_{7sec}$ (95% conf. limits) of the Compound in the rat yeast-paw test was determined to be 12.3 (5.7, 26.4)* mg/kg po at 30 minutes post-treatment.
*95% confidence limits

REFERENCES

Mouse Acetic Acid Writhing Test

Hendershot, L.C. and Forsaith, S.: Antagonism in the frequency of phenylquinone-induced writhing in the mouse by weak analgesics and non-analgesics. J. Pharmacol. Exp. Ther. 125:237–240, 1959.

Koster, R., Anderson, M. and DeBeer, E. J.: Acetic acid for analgesic screening. Fed. Proc. 18: 412,1959.

Litchfield, J. T., and Wilcoxon, F.: A simplified method of evaluting dose-effect experiments. J. Pharmacol. Exp. Ther. 96: 99–113, 1949.

Rat Yeast-Paw Test

Brownlee, K. A.: Statistical theory and methodology. In Science and Engineering, ed. by K. A. Brownlee, pp. 145–162, John Wiley & Sons, Inc., New York, 1965.

Chipkin, R. E., Iorio, L. C., Latranyi, M. B. and Barnett, A.: Direct analgesic effects of Z-prolyl-D-leucine and Z-prolyl-L-leucine in the rat yeast-paw test. J. Pharmacol. Exp. Ther. 226: 164–170, 1983.

Randall, L. O. and Selitto, J. J.: A method of measurement of analgesic activity on inflamed tissue. Arch. Int. Pharmacodyn Ther., 111: 409–419, 1957.

The compound of the invention and the pharmaceutically acceptable salts thereof are orally effective analgesic agents. The amount and frequency of administration will be requlated accordingly to the judgement of the attending clinician considering such factors as age, condition and size of the patient as well as severity of the symptom being treated. A typical recommended dosage regimen is oral administration of from 75 to 1200 mg/day, preferably 150 to 600 mg/day, in two to four divided doses to achieve relief of the symptoms.

The compound of the invention and the pharmaceutically acceptable salts thereof are also useful for treating inflammation. The anti-inflammatory use may be demonstrated by standard test procedures known in the art.

EXAMPLE 1

4,7-Dimethyl-2-(4-pyridinyl)-1,2,4-triazolo[1,5-a]pyrimidin-5(4H)-one

A mixture of 5-(methylamino)-3-(4-pyridinyl)-1H-1,2,4-triazole (10.5 gm) and ethyl acetoacetate (30.0 ml) was heated with stirring in an oil bath at 180° C. for 30 minutes. The mixture was cooled and ethanol (100 ml) was added. The solid material was collected by filtration and vacuum dried to give 13.3 gm of a mixture of isomers. This material was recrystallized three times from ethanol to give 4,7-dimethyl-2-(4-pyridinyl)-1,2,4-triazolo[1,5-a]pyrimidin-5(4H)-one, m.p. 195°–197° C., after vacuum drying at 100° C.

Anal. Calculated for $C_{12}H_{11}N_5O$: C, 59.74; H, 4.60; N, 29.03. Found: C, 59.48; H, 4.67; N, 29.35.

Alternatively, column chromatography of the mixture of isomers on silica gel and elution with ethyl acetate gave 4,7-dimethyl-2-(4-pyridinyl)-1,2,4-triazolo[1,5-a]pyrimidin-5(4H)-one, after recrystallization from ethanol and vacuum drying at 100° C. Elution with ethyl acetate:methanol (4:1) gave the isomeric product, 4,5-dimethyl-2-(4-pyridinyl)-1,2,4-triazolo[1,5-a]pyrimidin-7(4H)-one, m.p. 263°–267° C., after recrystallization from ethanol and vacuum drying. Anal. Calculated for $C_{12}H_{11}N_5O$: C, 59.74; H, 4.60; N, 29.03. Found: C, 59.58; H, 4.67; N, 29.24.

PREPARATIVE EXAMPLE 1

5-(Methylamino)-3-(4-pyridinyl)-1H-1,2,4-triazole

A solution of 4-pyridinecarboxylic acid 2-[(methylamino)iminomethyl]hydrazide (6.50 g) in aqueous 1N sodium hydroxide (45 ml) was heated at reflux for 2.5 hours. The solution was cooled in an ice bath and neutralized by addition of glacial acetic acid. The solid product was collected by filtration and vacuum dried to give 4.37 gm. Recrystallization from methanol and vacuum drying at 100° C. gave 5-(methylamino)-3-(4-pyridinyl)-1H-1,2,4-triazole. m.p. 228°–230° C. Anal. Calculated for $C_8H_9N_5$: C, 54.84; H, 5.18; N, 39.98. Found: C, 54.75; H, 5.15; N, 40.09.

PREPARATIVE EXAMPLE 2

4-Pyridinecarboxylic acid 2-[(methylamino)iminomethyl]hydrazide

Methylcarbamimidothioic acid methyl ester monohydriodide (33.0 gm) (prepared by the procedure given in Chem. Abst., 56,5831g, 1962), was added to cold aqueous 1N sodium hydroxide (142 ml). 4-Pyridinecarboxylic acid hydrazide (19.5 gm) was added to the cold solution with stirring. The reaction mixture was allowed to warm to room temperature and stirred for 72 hours. The solid product was collected by filtration, washed with a small amount of cold water and vacuum dried to give 24.0 gm. Recrystallization from methanol and vacuum drying at 100° C. gave 4-pyridinecarboxylic acid 2-[(methylamino)iminomethyl]hydrazide with m.p. 212°–215° C. dec.

Anal. Calculated for $C_8H_{11}N_5O$: C, 49.73; H, 5.74; N, 36.25. Found: C, 49.58; H, 5.63; N, 36.38.

The following formulations exemplify some of the dosage forms of the compositions of this invention. In each, the term "active compound" designates the compound, 4,7-dimethyl-2-(4-pyridinyl)-1,2,4-triazolo [1,5-a]pyrimidin-5(4H)-one or a pharmaceutically acceptable salt, solvate thereof.

Pharmaceutical Dosage Form Examples
Example A
Tablets

| No. | Ingredient | mg/tablet | mg/tablet |
|---|---|---|---|
| 1. | Active Compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Mix item nos. 1 and 2 in a suitable mixer for 10–15 minutes. Granulate the mixture with item no. 3. Mill the damp granules through a coarse screen (e.g., ¼") if needed. Dry the damp granules. Screen the dried granules if needed and mix with item no. 4 and mix for 10–15 minutes. Add item no. 5 and mix for 1–3 minutes. Compress the mixture to appropriate size and weight on a suitable tablet machine.

Example B
Capsules

| No. | Ingredient | mg/capsule | mg/capsule |
|---|---|---|---|
| 1. | Active Compound | 100 | 500 |
| 2. | Lactose USP | 106 | 123 |
| 3. | Corn Starch, Food Grade, | 40 | 70 |
| 4. | Magnesium Stearate NF | 4 | 7 |
|  | Total | 250 | 700 |

Method of Manufacture

Mix item nos. 1, 2 and 3 in a suitable blender for 10–15 minutes. Add item no. 4 and mix for 1–3 minutes. Fill the mixture into suitable two-piece hard gelatin capsules on a suitable encapsulating machine.

Example C
Parenteral

| Ingredient | mg/vial | mg/vial |
|---|---|---|
| Active Compound Sterile Powder | 100 | 500 |

Add sterile water for injection or bacteriostatic water for injection for reconstitution.

Example D
Injectable

| Ingredient | mg/vial | mg/vial |
|---|---|---|
| Active Compound | 100 | 500 |
| Methylparaben | 1.8 | 1.8 |
| Propylparben | 0.2 | 0.2 |
| Sodium Bisulfite | 3.2 | 3.2 |
| Disodium Edetate | 0.1 | 0.1 |
| Sodium Sulfate | 2.6 | 2.6 |

-continued

| | Example D Injectable | |
|---|---|---|
| Ingredient | mg/vial | mg/vial |
| Water for Injection q.s. ad | 1.0 ml | 1.0 ml |

Method of Manufacture

1. Dissolve parabens in a portion (85% of the final volume) of the water for injection at 65°–70° C.
2. Cool to 25°–35° C. Charge and dissolve the sodium bisulfite, disodium edetate and sodium sulfate.
3. Charge and dissolve drug.
4. Bring the solution to final volume by adding water for injection.
5. Filter the solution through a 0.22 membrane and fill into appropriate containers.
6. Terminally sterilize the units by autoclaving.

The relevant teachings of all published references cited herein are incorporated by reference.

We claim:

1. A method for treating pain in a mammal which comprises administering a pharmaceutical composition which comprises an analgesic effective amount of 4,7-dimethyl-2-(4-pyridinyl)-1,2,4-triazolo[1,5-a]pyrimidin-5(4H)-one, having the structural formula

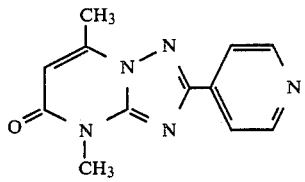

or the pharmaceutically acceptable salts thereof or a pharmaceutically acceptable solvate thereof in combination with a pharmaceutically acceptable carrier, to said mammal.

2. The method of claim 1 wherein the composition administered is in unit dosage form.

3. A method for treating pain in a mammal which comprises administering an effective amount of a pharmaceutical composition which comprises an analgesic effective amount of the dihydrate solvate of the compound defined in claim 1 in combination with a pharmaceutically acceptable carrier, to said mammal.

4. The method of claim 3 wherein the composition administered is in unit dosage form.

5. A method of treating inflammation in a mammal which comprises administering a pharmaceutical composition which comprises an anti-inflammatory effective amount of 4,7-dimethyl-2-(4-pyridinyl)-1,2,4-triazolo[1,5-a]pyrimidin-5(4H)-one, having the structural formula

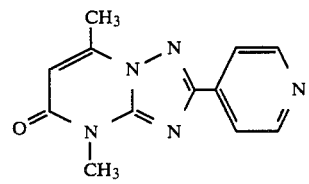

or the pharmaceutically acceptable salts thereof or a pharmaceutically acceptable solvate thereof in combination with a pharmaceutically acceptable carrier, to said mammal.

6. The method of claim 5 wherein the composition administered is in unit dosage form.

7. A method for treating inflammation in a mammal which comprises administering an effective amount of a pharmaceutical composition which comprises an anti-inflammatory effective amount of the dihydrate solvate of the compound defined in claim 5 in combination with a pharmaceutically acceptable carrier, to said mammal.

8. The method of claim 7 wherein the composition administered is in unit dosage form.

* * * * *